US00PP20689P3

(12) United States Plant Patent
Ballington et al.

(10) Patent No.: US PP20,689 P3
(45) Date of Patent: Jan. 26, 2010

(54) RASPBERRY NAMED 'NANTAHALA'

(50) Latin Name: ***Rubus idaeus* Linnaeus**
Varietal Denomination: Nantahala

(75) Inventors: James R. Ballington, Raleigh, NC (US); Gina E Fernandez, Raleigh, NC (US); Susan K. Bryson, Fletcher, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/998,754

(22) Filed: Jan. 15, 2008

(65) Prior Publication Data

US 2009/0183287 P1 Jul. 16, 2009

(51) Int. Cl.
*A01H 5/00* (2006.01)

(52) U.S. Cl. ..... Plt./204

(58) Field of Classification Search ..... Plt./204
See application file for complete search history.

*Primary Examiner*—Annette H Para

(57) ABSTRACT

*Rubus idaeus* Linnaeus 'Nantahala' is a new and distinct variety of raspberry that has the following unique combination of desirable features that are outstanding in a new variety.

1. Late season ripening to follow 'Heritage'.
2. Fruit is medium size, 3.5 g.
3. Fruit is firm, very attractive, uniform and conical to ovate.
4. Consistent and moderate yields.

2 Drawing Sheets

Latin name of the genus and species: The Latin name of the novel raspberry variety disclosed herein is *Rubus idaeus* Linnaeus.

Variety denomination: The inventive cultivar of *Rubus idaeus* disclosed herein has been given the variety denomination 'Nantahala'.

BACKGROUND OF THE INVENTION

The present invention related to a new and distinct cultivar of *Rubus idaeus* Linnaeus (raspberry) grown as a fruiting shrub for commercial agriculture. Raspberries are typically consumed both fresh and in a number of processed products.

The new and distinct variety of raspberry (*Rubus idaeus* Linnaeus) originated from the hand pollinated cross of 'NC 245' ('Algonquin'×'Royalty') (unpatented)×'Rossana' (unpatented) made in 1994 in Raleigh, N.C. 'NC 245' is a primocane fruiting red raspberry, with moderate vigor, low yield and poor fruit quality and taste. 'Rossana' is a primocane fruiting red raspberry with superior flavor but has low vigor in North Carolina climate. The seeds were germinated in the winter of 1994–1995 and the resulting seedlings were established at the Upper Piedmont Research Station in Reidsville, N.C. (GPS coordinates N36°, W0791') in the spring of 1995. When the seedlings had experienced 4 years of growth under field conditions in 1998, 'NC451' was selected for it large and firm berry and superior fruit flavor. The selection was then propagated by crown divisions and root cuttings in Raleigh, N.C. The propagules were planted in replicated trials with other raspberries at the Mountain Horticultural Research Station (GPS N35° W082') in Fletcher, N.C. and the Upper Mountain Research Station (GPS N36° W081') in Laurel Springs, N.C. Plants and fruit of this new variety have remained true to type through successive cycles of asexual propagation. The new variety has been named the 'Nantahala' cultivar.

'Nantahala' is adapted to western North Carolina. There has been no observed winter damage in our tests, therefore winter hardiness is unknown. Chilling requirement of 'Nantahala' is unknown.

SUMMARY OF THE INVENTION

'Nantahala' is a new and distinct variety of raspberry for fresh market production. 'Nantahala' berry is larger and firmer than 'Heritage' an industry standard. 'Nantahala' ripens later than most primocane fruiting cultivars and is recommended for the mountain regions of North Carolina and adjacent states with high elevation. In sensory evaluation panels, 'Nantahala' rated as good or better than 'Caroline', 'Heritage' and a store bought cultivar from California. In the Cherokee language, 'Nantahala' means "land of the midday sun."

BRIEF DESCRIPTION OF THE DRAWINGS

The photographs were made using digital photography techniques and illustrate the colors as true as reasonably possible when using these techniques. Colors in the photographs may differ slightly from the color values cited in the detailed botanical description, which accurately describe the colors of the new *Rubus idaeus* variety. All photographs were taken from plants grown at the Upper Mountain Research Station in Laurel Springs, N.C. which was established in April 2002. Photographs were taken Sep. 26, 2007.

DETAILED BOTANICAL DESCRIPTION OF THE VARIETY

The following is a detailed botanical description of a new and distinct variety of *Rubus idaeus* Linnaeus know as 'Nantahala'. The observations below are from mature plants grown in test plots at a standard spacing of row width of 2 feet and 10 feet between rows. Those skilled in the art of cultivar description and evaluation will appreciate that certain characteristics of a variety will vary with older or conversely younger plants, as well as plants grown under different production protocols. 'Nantahala' has not been observed under all possible environmental conditions. Where dimensions, sizes, colors and other characteristics are given, it is to be understood that such characteristics are approximations or averages set forth as accurately as possible. The phenotype of the variety may differ from the description herein with variations in the environment such as season, temperature, light intensity, day length and cultural conditions. Color notations are based on The Royal Horticultural Society Colour Chart, The Royal Horticultural Society, London, UK, 2007 edition.

Yield components for 'Heritage', 'Caroline' (U.S. Plant Pat. No. 10,412) and 'Nantahala' can be found in Table 1. For botanical description purposes, 'Nantahala' was compared to the earlier ripening 'Heritage' a full description can be found in Table 2.

TABLE 1

Yield components of raspberries harvested from Laurel Springs, and Fletcher, NC.

| | Laurel Springs, NC Yield estimate lbs/acre[1] | Laurel Springs, NC Berry Wt (g) | Fletcher, NC Yield estimate lbs/acre[1] | Fletcher, NC Berry Wt (g) |
|---|---|---|---|---|
| Nantahala | 8107 | 3.5 | 9253 | 3.5 |
| Caroline | 12306 | 3.2 | 12583 | 2.5 |
| Heritage | NA | NA | 10178 | 2.9 |

[1]Yields based on 3 years of replicated cultivar trials at each location, for a total of 6 years. Yield estimates were calculated using: Yield/cane of 3 canes/plot, * no. canes/plot. Yield estimation model from: Daubeny, H. A., A. Dale, , G. McGregor. 1986. Estimating yields of red raspberries in small research plots. HortScience: 21(5): 1216-1217.

The botanical descriptive data presented were collected from mature plants at the Upper Mountain Research Station in Laurel Springs, N.C. in 2006 and 2007. Table 2 provides information on the plant and fruit characteristics of the new cultivar 'Nantahala'. The new variety is particularly characterized and distinguished from other cultivars by its medium size, conical-ovate shape and attractive firm fruit with moderate, late and consistent yields.

TABLE 2

Plant and fruit characteristics of 'Nantahala' and 'Heritage'.

| | 'Nantahala' | 'Heritage' |
|---|---|---|
| General | | |
| Plant size (cm) | 151 | 126 |
| Growth habit | Erect | Erect |
| Productivity | Low-Medium | Medium |
| Self-fruitfulness | Self | Self |
| Time of bud burst (Raleigh NC) | 1-Apr | 29-Mar |
| Primocane fruiting | | |
| Percent of cane length flowering as primocane | 25 | 30 |
| Percent of total yield | 90 | 85 |
| Number of fruiting nodes | 9-11 | 14-15 |
| Primocanes | | |
| Number of young shoots/ft2 | 12 | 8 |
| Length (cm) | 151 | 126 |
| Cane diameter at 15 cm from ground (cm) | 8.1 | 7.6 |
| Cane diameter at 50 cm from ground (cm) | 7.5 | 6.8 |

TABLE 2-continued

Plant and fruit characteristics of 'Nantahala' and 'Heritage'.

| | 'Nantahala' | 'Heritage' |
|---|---|---|
| Height: diameter at 15 cm from ground | 19.1 | 16.5 |
| Height: Diameter at 50 cm from ground | 20.9 | 18.8 |
| Time of shoot emergence | 3-Apr | 31-Mar |
| Glaucosity (waxy bloom) | Weak | Weak |
| Cane cross section from mid cane of primocane | Round | Round |
| Dormant cane color | 167C | 183B |
| Prickles | | |
| Pigmentation | 183A | 178A |
| Density on young shoots | Moderate | Dense |
| Attitude of tip | Straight | Down |
| Texture | Smooth | Rigid |
| Presence and distribution on petioles | Present and irregular | Present and irregular |
| Pubescence on canes | Absent | Absent |
| Internodal distance (cm) at central ⅓ of cane | 2.3 | 3.2 |
| Density per 1 cm cane at 15 cm from ground | 17 | 17 |
| Density per 1 cm cane at 50 cm from ground | 5 | 6 |
| LEAVES | | |
| Face color | 137A | 137A |
| Relief between veins | Weak | Very weak |
| Glossiness | Medium | Medium |
| Underside color | 148B | 148B |
| Petiole Length (cm) | 4.9 | 5.9 |
| Stipule orientation | Erect | Erect |
| Arrangement | Compound | Compound |
| Number of leaflets | 3, 5 sometimes | 3, 5 sometimes |
| Overlapping of lateral leaflets | Free to touching | Free to touching |
| Lateral leaflet: length of stalklet | Very short | Very Short |
| Terminal leaflet | | |
| Length (cm) | 13.5 | 16.5 |
| Width (cm) | 15 | 17.9 |
| Shape | Ovate | Ovate |
| Tip | Acuminate | Acuminate |
| Margin | Double serrate | Double serrate |
| Lateral leaflets (basal pair) | | |
| Length (mm) | 87 | 92 |
| Width | 57 | 54 |
| Overlap | Touching | Touching |
| Orientation | Opposite | Opposite |
| Shape | Ovate | Ovate |
| Tip | Acuminate | Acuminate |
| Base | Acute to rounded | Acute to rounded |
| Margin | Double serrate | Double serrate |
| FLOWERS | | |
| Flowering period | | |
| Primocane | Aug. 15-Sep. 15 | Aug. 1-Sep. 1 |
| Floricane | Not harvested | Not harvested |
| Flower diameter (mm) | 18 | 17 |
| Fragrance | No distinguishing fragrance was noted | No distinguishing fragrance was noted |
| Petal | | |
| Length | 6.3 | 6.3 |
| Width | 2.7 | 2.7 |
| FRUIT | | |
| Harvest season | | |
| Primocane | 9/15 to frost | 9/1 to frost |
| Floricane | Unknown | Unknown |
| Number of fruiting laterals | 8 | 12 |

TABLE 2-continued

Plant and fruit characteristics of 'Nantahala' and 'Heritage'.

| | 'Nantahala' | 'Heritage' |
|---|---|---|
| Length ($4^{th}$ lateral from tip) (cm) | 9 | 7 |
| Number of fruit per lateral | 6 | 8 |
| Color | | |
| Immature | 47B | 42B |
| Maturing | 46A | 46A |
| Mature fruit | 59A | 59A |
| Glossiness | Medium | Medium |
| Shape | Conical-ovate | Ovate |
| Dimensions | | |
| Length (mm) | 21 | 17 |
| Width (mm) | 19.8 | 15 |
| Length: width | 1.06 | 1.13 |
| Weight (g/fruit) | 3.5 | 2.9 |
| Soluble solids | 10.8 | 9 |
| Seed weight (g) | 0.002 | 0.008 |
| Number of drupelets/fruit | 70 | 100 |
| Adherence to plug | Medium | Medium |
| Firmness | Medium to Firm | Medium |
| Yield | Low to medium | Medium |

Sensory Evaluation of Nantahala and 4 other red raspberries, 'Caroline', "California" (bought off the shelf), and 'Heritage' were conducted at the NCSU Dept. Food Science in 2006 (Table 3). 'Nantahala' scored as good or better than other cultivars in overall liking, appearance (shape and color), flavor, texture and seediness.

TABLE 3

Sensory Evaluation of 'Nantahala' and three other primocane fruiting red raspberries[1].

| Question Title | Attribute | Nantahala | | Caroline | | "California" | | Heritage | |
|---|---|---|---|---|---|---|---|---|---|
| Overall Liking | Overall | 6.39 | a* | 5.68 | a | 5.77 | a | 5.84 | a |
| Appearance Liking | Red Color | 7.39 | a | 6.56 | bc | 6.53 | bc | 5.89 | c |
| Appearance Liking | Shape | 7.23 | a | 6.05 | c | 7.14 | a | 6.26 | bc |
| Flavor Liking | Flavor | 6.07 | a | 5.7 | a | 5.61 | a | 5.49 | a |
| Texture Liking I | Firmness | 6.16 | a | 4.88 | b | 6.49 | a | 5.81 | a |
| Texture Liking I | Juiciness | 6.67 | ab | 5.93 | b | 6.04 | ab | 6.16 | ab |
| Seediness/Fuzziness | Seediness | 2.96 | a | 2.54 | b | 2.49 | b | 2.74 | ab |
| Seediness/Fuzziness | Fuzziness | 2.18 | b | 2.07 | b | 2.79 | a | 2.32 | b |

*Means in a row followed by different letters are significantly different at the $p < 0.05$ level

[1]Sensory Evaluation Method (NCSU Dept. Food Science)
Consumers scored all products for overall acceptability, red color, shape, flavor, firmness, juiciness, seediness and fuzziness on a 9-point hedonic scale where 9 = like extremely and 1 = dislike extremely.

That which is claimed is:

1. A new and distinct variety of commercial red raspberry plant (*Rubus idaeus* Linnaeus) substantially as illustrated and described, characterized by its medium size conical-ovate shaped and attractive firm fruit, with moderate, late and consistent yields.

* * * * *

Fig. 1 shows typical fruit of 'Nantahala'.
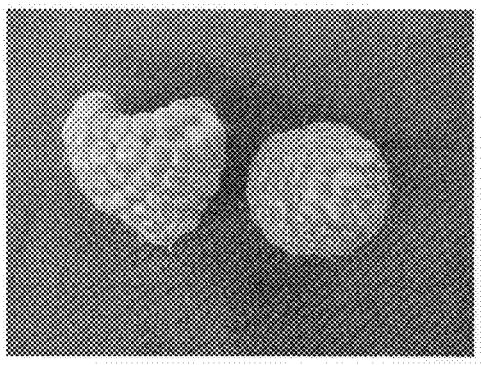
Fig. 2 shows the typical fruit of 'Nantahala' compared to 'Heritage'
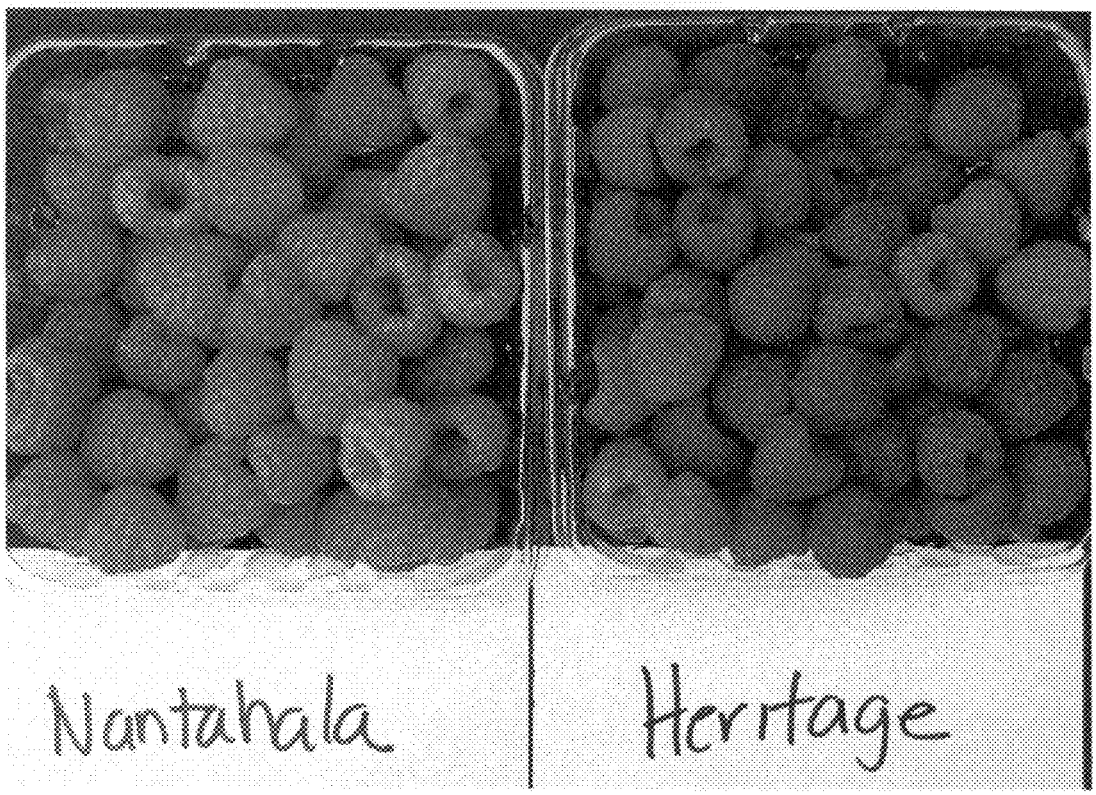

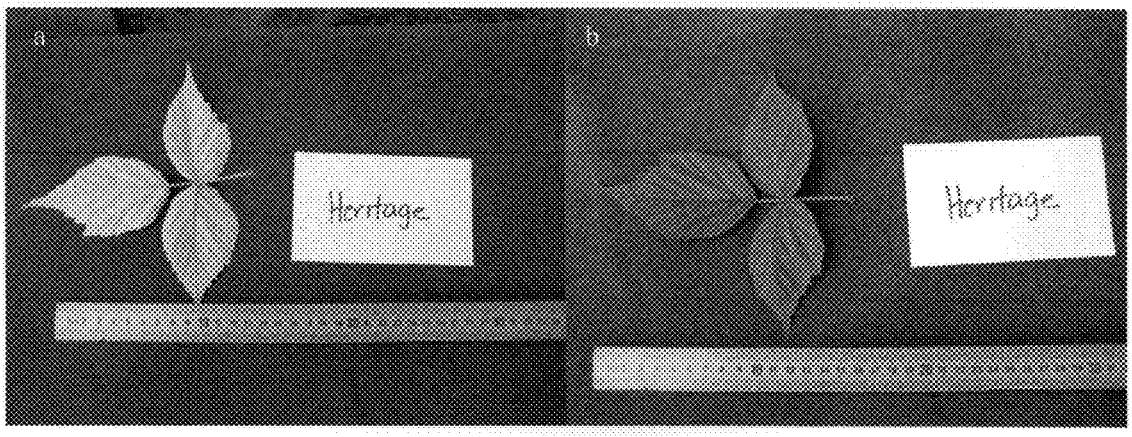

Fig. 3a and b. Shows abaxial (lower) and adaxial (upper) surfaces of primocane leaves of 'Nantahala' raspberry.
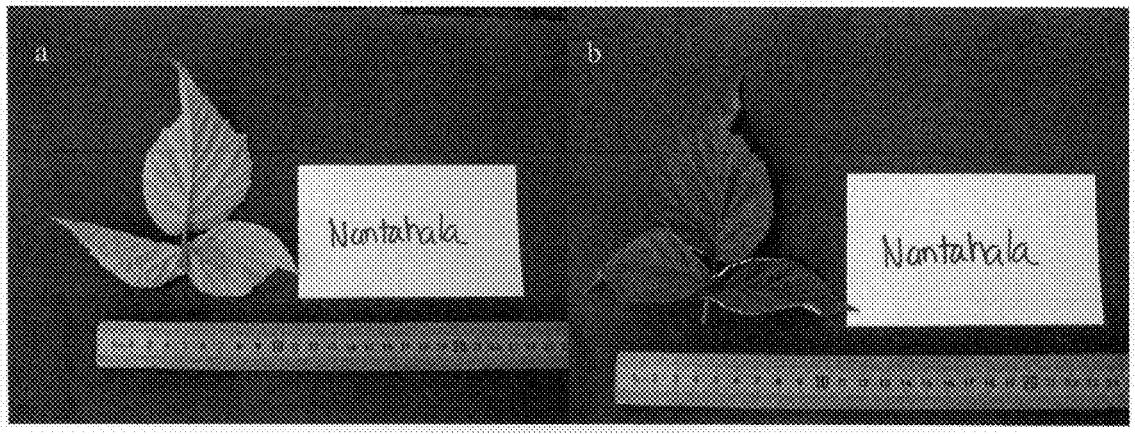
Fig. 4a and b. Shows abaxial (lower) and adaxial (upper) surfaces of primocane leaves of 'Heritage' raspberry.